United States Patent [19]

Bruckner et al.

[11] 4,267,149
[45] May 12, 1981

[54] EVALUATION INSTRUMENT FOR AUTOMATIC PHOTOMETRIC ANALYSIS OF LIQUID SAMPLES

[75] Inventors: Elmar Bruckner, Bischberg; Hans Gausmann, Aalen; Philipp Schipper, Erlangen; Walter Tausch, Aalen, all of Fed. Rep. of Germany

[73] Assignee: Carl Zeiss-Stiftung, Oberkochen, Fed. Rep. of Germany

[21] Appl. No.: 8,038

[22] Filed: Jan. 31, 1979

[30] Foreign Application Priority Data

Feb. 4, 1978 [DE] Fed. Rep. of Germany ....... 2804881

[51] Int. Cl.³ .................... G01N 35/02; G01N 33/50; G01N 21/11
[52] U.S. Cl. ........................................ 422/65; 422/61; 422/67; 250/577; 356/246; 364/498
[58] Field of Search .................. 422/61, 65, 67, 68; 364/497, 498; 356/39, 246; 250/577

[56] References Cited

U.S. PATENT DOCUMENTS

| | | | |
|---|---|---|---|
| 3,476,515 | 11/1969 | Johnson et al. | 422/61 X |
| 3,497,320 | 2/1970 | Blackburn et al. | 422/61 X |
| 3,504,376 | 3/1970 | Bednar et al. | 422/61 X |
| 3,554,705 | 1/1971 | Johnston et al. | 422/61 |
| 3,703,336 | 11/1972 | Rosse et al. | 356/246 |
| 4,106,671 | 8/1978 | Sharples | 250/577 |
| 4,134,022 | 1/1979 | Jacobsen | 250/577 |
| 4,156,149 | 5/1979 | Vacari | 250/577 |

FOREIGN PATENT DOCUMENTS

| | | |
|---|---|---|
| 1673350 | 9/1971 | Fed. Rep. of Germany . |
| 2040481 | 2/1972 | Fed. Rep. of Germany . |
| 7241230 | 5/1974 | Fed. Rep. of Germany . |
| 526109 | 9/1972 | Switzerland . |

*Primary Examiner*—R. E. Serwin
*Attorney, Agent, or Firm*—Hopgood, Calimafde, Kalil, Blaustein & Lieberman

[57] ABSTRACT

The invention contemplates instrumentation to enable performance of a plurality of automatic photometric analyses upon liquid samples, as in different analyses of such body fluids as blood, urine, etc. Prior to photometric evaluation, the liquid samples are automatically subjected to controlled doses of one or more reagents, and dwell times, as appropriate to the analysis to be performed at any given time. The particular automatic performance of a given analysis is supplied from an insertably replaceable holder which contains the reagents, dosage devices, and program-control coding unique to the particular analysis. Upon inserted replacement of the holder with another selected holder which is suitably encoded and equipped with reagents, the same instrument will serve for the handling of liquid samples unique to a different biological analysis.

11 Claims, 5 Drawing Figures

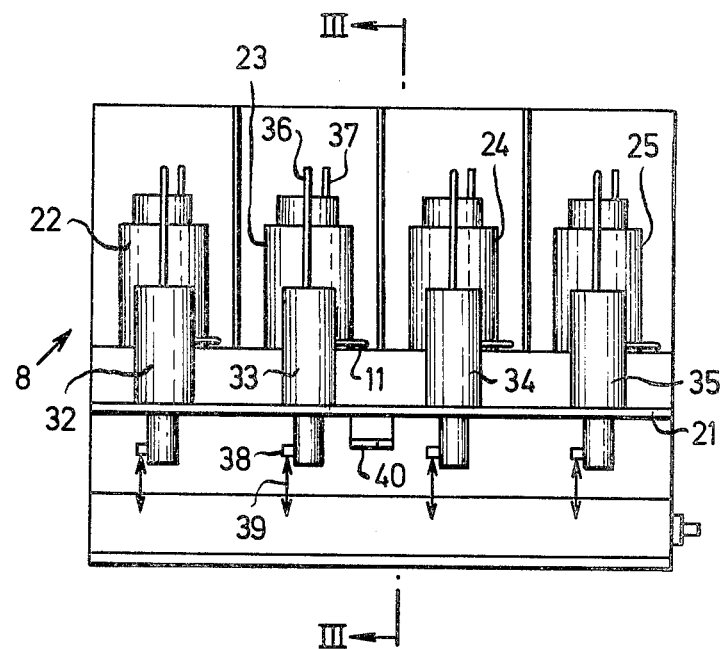
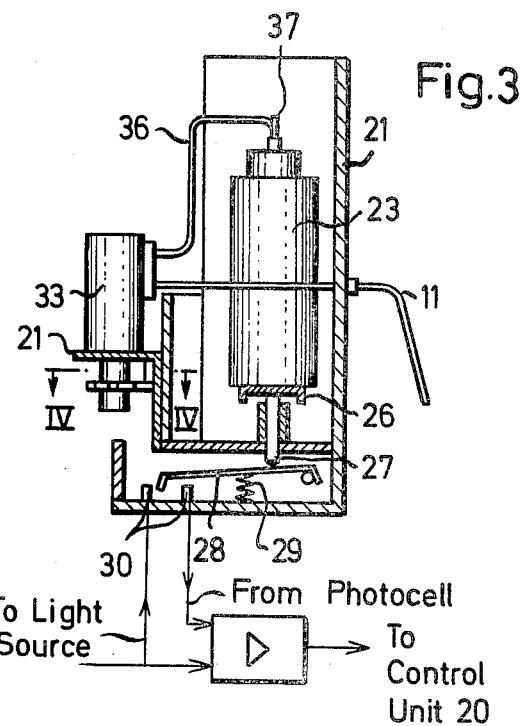
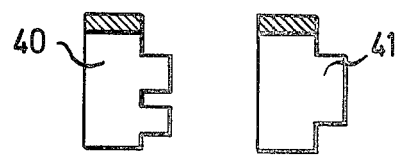

EVALUATION INSTRUMENT FOR AUTOMATIC PHOTOMETRIC ANALYSIS OF LIQUID SAMPLES

BACKGROUND OF THE INVENTION

The present invention relates to an evaluating instrument for the automatic photometric analysis of liquid specimens in which reagents appropriate for the specific analysis are supplied in predetermined doses to the specimen to be measured, and in which the actual measurement is effected with instrument parameters adapted to the specific analysis.

Such evaluation instruments are used, in particular, for the analysis of body fluids such as blood, urine, etc., their purpose being to carry out a plurality of analyses within a short time and without the need for trained medical personnel.

Several such automatic analyzers are known. Thus, an instrument is known in which fluid to be analyzed is conducted through a labyrinth of flexible tubes, whereby a given number of different analyses are necessarily performed. This device has the disadvantage that a fixed path for the sample and a fixed sequence of analysis are pre-established so that it is not possible to select the number and sequence of the analyses as desired. The instrument can therefore not operate selectively.

An automatic analyzer is also known (Swiss Pat. No. 526,109) which operates with the use of punched cards and on which there are firmly arranged containers which contain in completely dosaged amount all reagents necessary for a given analysis as well as a reaction chamber. Each of these punch cards bears a coding. If a given analysis is to be carried out with a sample, the punched card in question is inserted into the evaluation instrument. There, a predetermined amount of specimen is injected into the reaction chamber, and at the same time all reagents present pass from their storage containers into the reaction chamber. The adjustment of the instrument parameters, and thus the measurement, takes place in accordance with the coding of the punched card. The measured value is stored on the punched card and subsequently evaluated.

Evaluation instruments of the latter type can operate selectively, but they are limited in their possibilities of application since it is not possible freely to select the reagents. Furthermore, their operation is expensive, since a separate punched card with completely predosed reagents is necessary for each individual measurement. Finally, the accuracy of the individual measurement is limited, due to the fact that each measurement must be carried out at a different reaction chamber, as a result of which homogeneity is not assured for light-penetration of specimen chamber walls, and a reduction of measurement light is possible.

SUMMARY OF THE INVENTION

The object of the present invention is to provide an evaluation instrument for the automatic photometric analysis of liquid specimens (1) which, with free selection of the reagents, makes possible a simple selective switching from one method of analysis to another, (2) which requires only a minimum expense for the performance of each analysis, and (3) which produces accurate measurement results.

According to the present invention, this object is achieved, in an instrument of the character indicated, by means of an insertably replaceable holder having a separate container for each of the reagents necessary for the analysis, having a separate metering pump uniquely set to deliver a requisite dose of the reagent from each container, and having a readable-code indicium which, upon holder insertion, cooperates with code-sensing means on the instrument to establish an automatic control and evaluation program involving addition of reagents, dwell time or times, and supply to a photometer, as necessary for the analysis. More specifically, pump drives fixed to and therefore forming part of the instrument have coupled engagement with the metering pumps upon insertion of the holder; and a cell is arranged in the path of the photometer measurement beam to receive prepared samples.

By inserting the holder in the evaluation instrument, a given method of analysis is selected. Precise doses of necessary reagent are then taken from the containers via the metering pumps, this process being repeated for a plurality of successive samples. Coding on the inserted holder establishes the correct control and evaluation program for the particular analysis, so that the correct analysis procedure—involving specimen preparation and incubation with one or more reagents, measurement, and evaluation—is performed automatically. The measurement itself takes place in a cell in the photometer part of the instrument, entrainment errors being avoided in known manner, by interposition of flushing processes. The cell itself is optimally adapted to the measurement, so that the measurement results obtained are accurate and comparable.

In order to select a second (and different) method of analysis, the holder is merely replaced by a different one, uniquely equipped and encoded for the different method of analysis. In this way, the necessary reagents of the second method are available and their dose, as well as the control and evaluation program necessary for this method, are established; the measurement cell contained within the photometer part remains the same.

Since a large number of identical analyses can be carried out with one holder, it is advantageous to provide, within the holder, means for measuring how full the reagent containers are. As soon as these means respond and indicate a lack or inadequate supply of reagent, it is only necessary to replace the reagent container in question with a new one having a fresh supply of reagent.

It is advisable to develop the metering pumps in the holder in such a manner that they convey a predetermined volume of reagent upon each actuation, i.e., one dose per actuation. This permits a particularly simple development of requisite coupling to each of the pump drives forming part of the instrument.

The holder provided in the evaluation instrument of the invention is advantageously developed such that its reagent containers, its metering pumps, and an element which carries its coding are all replaceable. Thus, it is possible in very simple manner to re-equip the holder for different methods of analysis, and in particular also to use every newly developed method of analysis with the particular reagents which correspond to and are needed to perform the new method.

DESCRIPTION OF AN ILLUSTRATIVE EMBODIMENT

The invention will be described in further detail below with reference to FIGS. 1 to 4 of the accompanying drawings, in which:

FIG. 2 is a rear view in elevation showing an embodiment of a removable reagent holder for selectively inserted use in the instrument of FIG. 1;

FIG. 3 is a sectional view, taken along the line III—III of FIG. 2;

FIG. 4a is an enlarged sectional view of a coding-tab part of FIG. 3, being taken along the line IV—IV of FIG. 3; and FIG. 4b is a view similar to FIG. 4a, to show a different coding tab, for a different method of analysis.

Figure 1:
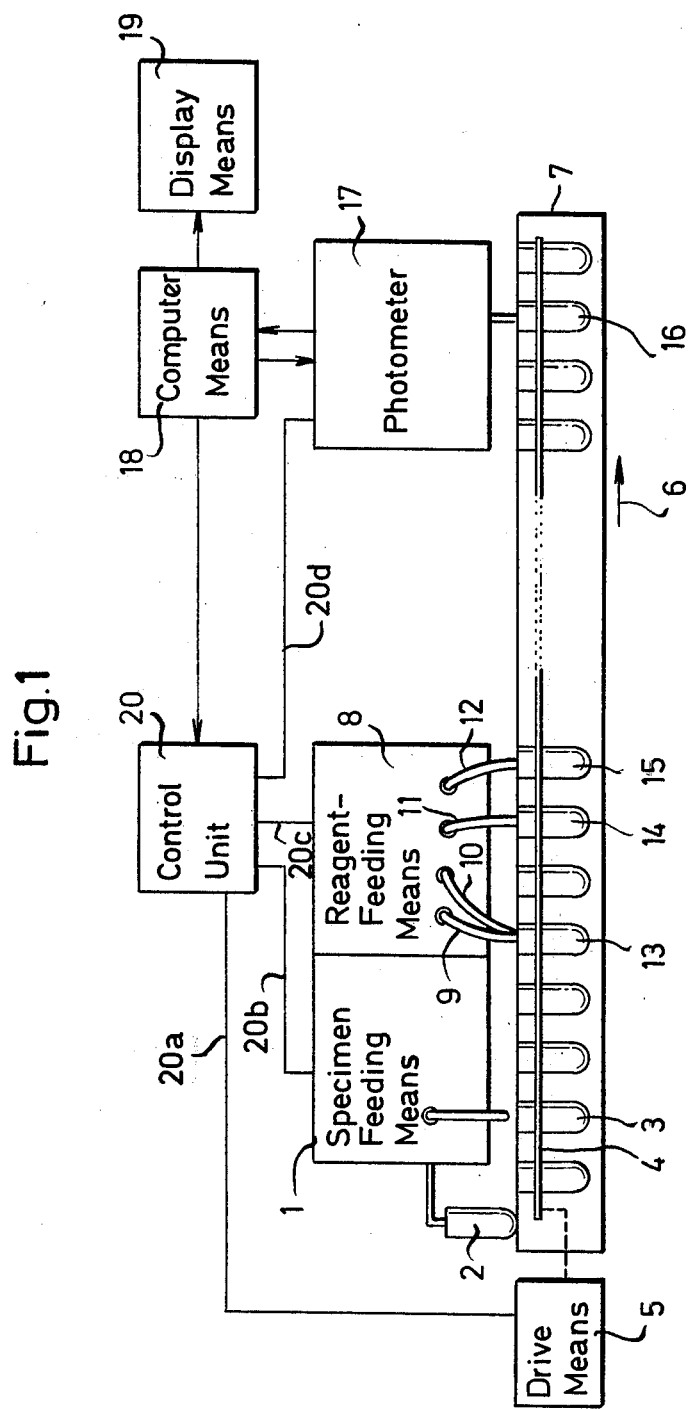
FIG. 1 is an overall diagram schematically showing the new evaluation instrument of the invention.

In FIG. 1, specimen-feeding means 1 serves to transfer into a specimen vessel 3 a predetermined volume of a specimen contained in the container 2 and a predetermined volume of a dilution solution. The single specimen container 2 will be understood to be but one of several containers, for example, with test fluid from several patients. And in the drawing, the showing of the specimen-feeding means 1 will be understood to have been greatly simplified; it can, for instance, be developed in the manner described and shown in German Offenlegungschrift No. 1,673,350.

The specimen vessel 3 is mounted, together with a large number of other vessels, on a conveyor belt 4 which is moved intermittently by drive means 5, belt movement of specimen vessels being within an enclosed device or reaction chamber 7 and in the direction indicated by an arrow 6.

Reagent-feeding means 8 serves to feed reagents to specimen vessels in required doses, and at proper times and places, as may be required for carrying out a given method of analysis. In the present example, the device 7 has four flexible feed lines 9, 10, 11, 12 for feeding four different reagents; these lines are shown positioned to feed different reagents into the specimen vessels 13, 14, 15.

As soon as a specimen vessel has reached the position 16, the liquid contained therein is fed to the cell of a photometer 17 and is measured there. Such feeding of the liquid to the measurement cell may be effected, for instance, by such suitable means as that described and shown in German Pat. No. 2,040,481.

The measurement result passes from the photometer 17 to computer means 18 and from there to display means 19. Computer means 18 serves at the same time to determine, via a control unit 20, the control and evaluation program corresponding to a given method of analysis. To this end, control unit 20 is shown with various control connections 20a, 20b, 20c, 20d to determine the timing and other operation of necessary cooperating functions at means 5, 1, 8 and 17, respectively.

The means 8 for feeding reagent is shown in further detail in FIGS. 2 and 3. It consists of a removable holder 21 in which reagent containers 22, 23, 24, 25 are inserted. Each of these containers rests on a scale which is shown in cross section in FIG. 3 for the container 23. The container 23 rests on a plate 26 which is connected to a pin 27. The pin presses against a pivoted tongue 28 which is urged upward by a spring 29. As soon as liquid in container 23 drops below a predetermined minimum, tongue 28 is raised by spring 29 to such an extent that a flange at its front end no longer interrupts a light beam between spaced elements 30, and the latter responds to signal an insufficiency of reagent, for example with a shut-down or other signal to control unit 20, as suggested by legend in FIG. 3.

The holder 21 is further provided with four dose-metering pumps 32, 33, 34, 35. Each of these pumps is connected via a flexible hose with its associated reagent vessel; for instance, pump 33 is connected with vessel 23 via hose 36. Further hoses, as at 37, serve for venting the respective reagent vessels. The outlet ports of the pumps are connected with the respective hoses 9 to 12 which have already been noted in FIG. 1.

The metering pumps are provided with lateral pins, as at 38 which, upon insertion of holder 21 at 8 in the evaluation instrument of FIG. 1, engage with drive motors secured to the instrument. Pumps 32 to 35 may, for example, be as described and shown in German Gebrauchsmuster Pat. No. 7,241,230. Such pumps extract a predetermined volume of liquid from the associated vessel 23 upon upward movement of pin 38 until it hits a stop, and upon downward movement of pin 38 the predetermined volume of said liquid is delivered into the associated discharge hose (e.g., 11). The drive motors, which are mounted to the instrument need therefore only effect a precise upward and downward movement of the pin 38, said motors and their drive motion being suggested by double arrows, as at 39 in FIG. 2.

A coded tab 40 is secured to and forms part of holder 21, such that, upon insertion of the holder into the evaluation instrument, the code profile at 40 cooperates with a suitable code-sensing device which is secured to and is therefore a fixed part of the instrument. The coding of tab 40 will be understood to be specific to the method of an analysis requiring particular reagents at 22, 23, 24, 25. Thus, it will be understood that, by sensing the code at tab 40, a part of the control program which is specific to the method is called up in the computer 18 and will, via the control unit 20, determine the entire course of the analysis, i.e., the quantity of specimen, the sequence of the addition of the reagents, the dwell or incubation time of the specimen vessels in the device 7, and finally the transfer to photometer 17. At the same time, the evaluation program will have been stored in the computer 18.

FIG. 4a shows a coding tab 40 which may control the sequencing and selection of events in automatically performing the analytical method, "Determination of Total Protein", wherein numerous successive specimens are subjected to the same method of analysis. And it will be understood that the subprogram associated with the analysis program coded at 40 may also determine how many flushing processes are to occur between measurements in the cell of the photometer 17, and how often the calibration is to be checked at 17 against a standard or reference solution. If it is desired to carry out other methods of analysis, for instance "Determination of Urea", another holder 21 equipped with other reagents and metering pumps is inserted, said other holder being equipped, for instance, with its coded tab 41 (FIG. 4b) unique to the procedure of such other method of analysis.

Thus, it is seen that, with suitably equipped and selectively inserted holders 21, it is possible without expense and very rapidly to use the single evaluation instrument of FIG. 1 for a large number of analytical methods.

The described evaluation instrument will be seen to provide means for effecting successive analytical determinations of uric acid, cholesterol, bilirubin, glucose, etc. By simple replacement of the reagents and of the metering pumps, or by corresponding dosage adjustment of existing metering pumps and by replacing the coding tab, each holder 21 can be re-equipped or reconstituted for a new, previously unplanned method of analysis.

More specifically, and for example, if holder 21 is suitably provisioned with reagents, dosage adjustments, placement of delivery hoses 9, 10, 11, 12, and is equipped with coding tab 41, the determination of urea proceeds automatically, in accordance with the following succession of events:

(a) Removal of 20 μl serum from container 2, with addition of 150 μl dilution;
(b) Addition of reagent A at vessel location 13;
(c) Incubation time of 15 minutes;
(d) Addition of reagent B at a predetermined vessel position between locations 15 and 16;
(e) Incubation time of 15 minutes;
(f) Measurement in the photometer 17.

Many analytical methods operate with but one or two reagents. However, in order to provide inherent capacity to perform all methods, the removable holder 21 is preferably provided with space for our reagent containers and four metering pumps, as shown.

What is claimed is:

1. An evaluation instrument for the automatic analysis of a liquid specimen pursuant to a prescribed analysis program, said instrument comprising a specimen container, a specimen vessel, intermittently operative conveyor means for indexing the specimen vessel into consecutive positions, specimen-feeding means having an inlet connection to said specimen container and a discharge outlet at one of said positions for transferring to said specimen vessel when in said one position a predetermined volume of a liquid specimen from said specimen container, reagent-feeding means at another of said positions for supplying to said specimen vessel when in said other position a predetermined reagent dose, the reagent dose having been selected in accordance with the specific analysis to be performed, photometer means for measuring the specimen with instrument parameters adapted to the specific analysis, specimen-transfer means associated with said photometer means and operative at a further conveyor position to transfer reagent-mixed specimen liquid from said specimen vessel to said photometer means upon indexed displacement to said further position; said reagent-feeding means comprising a replaceably disposed holder having a plurality of different reagent containers for the respective different reagents necessary for the specific analysis, a separate metering pump associated with each reagent container and operative to transfer reagent from a particular reagent container to said specimen vessel, said holder incuding pre-coded means unique to the specific analysis to be performed; and control means having a synchronizing connection to said conveyor means and a code-reading relation to the pre-coded means of an installed holder, as well as actuating connections to said specimen-feeding means and to said reagent-feeding means and to said photometer means, for determining the entire course of the specific analysis prescribed by said pre-coded means.

2. The evaluation instrument of claim 1, characterized by the fact that said holder includes means for measuring the height to which the reagent containers are filled, said last-defined means producing an output signal to said control means in response to a measurement of predetermined insufficiently filled height.

3. The evaluation instrument of claim 1, characterized by the fact that the reagent containers, the metering pumps, and the pre-coded means are replaceable.

4. The evaluation instrument of claim 1, characterized by the fact that the metering pumps are adapted in each case to pump a predetermined volume of reagent upon each actuation.

5. The evaluation instrument according to claim 1, characterized by the fact that four reagent containers and four metering pumps are arranged in said holder.

6. The evaluation instrument of claim 1, in which said specimen vessel is one of a plurality at conveyor spacings which correspond to indexing displacement of said conveyor means.

7. The evaluation instrument of claim 6, in which the metering pump associated with one of said reagent containers is positioned for discharge into a specimen vessel at one of a plurality of conveyor-indexed positions spanned by said reagent-feeding means, and in which the metering pump associated with another of the reagent containers is positioned for discharge into a specimen vessel at another of the positions spanned by said reagent-feeding means.

8. The evaluation instrument of claim 6, in which the respective metering pumps associated with two different reagent containers are positioned for independent discharge into a specimen vessel at a single conveyor-indexed position.

9. The evaluation instrument of claim 1, in which said conveyor means is part of an enclosed reaction chamber which extends between said reagent-feeding means and said specimen-transfer means.

10. The evaluation instrument of claim 2, in which said last-defined means produces an output signal to said control means in response to a measurement of predetermined insufficiently filled height.

11. As an article of manufacture, a unit-handling reagent-feeding holder for selective removable insertion in evaluation instrumentation which includes a code-reading control device and an indexing conveyor of liquid-specimen vessels over a path of movement from a first station of discharging reagent into one or more specimen vessels to a second station of photometer measurement; said holder comprising a plurality of reagent containers respectively adapted to contain different reagents necessary for a particular analysis program, a corresponding plurality of reagent pumps each of which is associated with the outlet of a different reagent container and each of which is adapted in response to a control actuation to discharge into an adjacent specimen vessel a predetermined volume of reagent from the associated reagent container, and readable means encoded uniquely to a particular desired evaluation and adapted for code-reading coaction with the control device of the evaluation instrumentation; whereby an operation of the evaluation instrumentation may be controlled in accordance with the encoding of said readable means, such controlled operation being unique to the evaluation for which the particular holder is pre-characterized.

* * * * *